United States Patent [19]
Godin

[11] 3,990,853
[45] Nov. 9, 1976

[54] LIQUID TRANSFER VALVE STRUCTURE

[75] Inventor: Thomas J. Godin, West Hollywood, Fla.

[73] Assignee: Coulter Electronics, Inc., Hialeah, Fla.

[22] Filed: May 30, 1975

[21] Appl. No.: 582,307

[52] U.S. Cl. ............................. 23/259; 73/422 R; 23/253 R; G01N/1/18
[51] Int. Cl.² ..................... G01N 1/10; G01N 1/16; G01N 1/18
[58] Field of Search ................ 23/259, 253, 230 B, 23/254 R; 73/422

[56] References Cited
UNITED STATES PATENTS

| | | | |
|---|---|---|---|
| 2,846,121 | 8/1958 | Ronnebeck | 222/133 |
| 3,362,228 | 1/1968 | Stuben | 73/422 |
| 3,567,389 | 3/1971 | Coulter et al. | 23/259 |
| 3,567,390 | 3/1971 | Rothermel | 23/259 |
| 3,615,241 | 10/1971 | Low | 23/253 X |
| 3,819,330 | 6/1974 | Creighton | 23/254 X |

*Primary Examiner*—R.E. Serwin
*Attorney, Agent, or Firm*—Silverman & Cass, Ltd.

[57] ABSTRACT

A pneumatically operated liquid transfer valve structure formed of a pair of stationary elements sandwiching a slidably movable element which includes a two pair of spaced parallel arranged through passageways of precise known volume oriented normal to the direction of travel of the slidable element, said passageways adapted to communicate alternately between aligned ones of the two pair of similar passageways formed in each of the stationary elements and arranged axially aligned. The slidably movable element is propelled to its reciprocal positions by fluid pumps each of which includes a cylinder having a flexible diaphragm and a reciprocable plunger mounted on a piston. Each pump is arranged on opposite ends of the valve elements. The free ends of the plungers are arranged selectively to engage one or the other ends of the slidable element at the limits of its path of travel. Each pump includes entry and outlet ports, an interior cavity, and a flexible diaphragm mounted at the mouth of said cavity and adapted to be flexed by introduction of positive pressure depending upon the flow of fluid into or out of said cavity, the flexing of said diaphragm effecting a pressure applied to said movable member whereby to drive the plunger so that at one end force is applied thereby against the slidable element to translate same between the pair of selected positions. The opposite plunger is forced or otherwise withdrawn from the path of such element at the same time, causing the plunger of the opposite cylinder to assume an initiate condition so as to ready the same in condition for return.

37 Claims, 7 Drawing Figures

LIQUID TRANSFER VALVE STRUCTURE

BACKGROUND OF THE INVENTION

1. Field of the Invention

This invention relates generally to liquid transfer systems and more particularly provides a pneumatically operated liquid transfer valve having a linearly movable valve element carrying measuring passageways oriented to effect gravity induced drainage.

2. Description of the Prior Art

In the U.S. Pat. No. 3,549,994, there was provided a structure in which a sample of blood is driven into a fluid system in which it is accurately diluted with a suitable diluent and divided into two samples for red and white blood cell determination. The red sample for red cell determination is counted and sized utilizing a COULTER scanning device and is discharged, while at the same time the other is lysed to break up the red cells and subjected to another COULTER electronic scanning device for a white cell count with the simultaneous examination of the sample for hemoglobin determination and discharge. Processing is automatic and continuous for samples drawn into the apparatus at intervals exceeding at least a certain minimum time duration. The structure therein disclosed included means for combining the data automatically to ascertain certain of the parameters which are susceptible of derivation for determinations made, and producing data corresponding to all of the parameters both determined and derived from the apparatus. These parameters were blood counts, sizes, percentages, and the like, accepted in the medical arts as aids for diagnosis, treatment, and research. The structure therein disclosed utilized vessels, valves, and connecting conduits for the intermixing and/or diluting of fluids primarily for the purpose of making measurements and tests on such fluids. Of course, it should be appreciated that such description is somewhat general and while primarily utilized with an automatic instrument such as disclosed in the above-identified patent and employs the particle analyzing apparatus of the type disclosed in U.S. Pat. No. 2,656,508, it is capable of many uses. In medicine, biology, chemistry, and allied fields, research as well as routine testing required the use of apparatus which can produce fluid mixtures of specific concentrations accurately and automatically and particularly, can feed known quantities of fluids to a selected one of a plurality of locations.

In the apparatus referred to in U.S. Pat. No. 3,549,994, samples of whole blood were introduced one every fifteen seconds. The apparatus performs the requisite dilutions, tests, and computations needed for obtaining blood counts of white and red cells, a hematocrit determination, a hemoglobin measurement, and so on. Accordingly, such automatic instrument is required quickly and accurately to prepare the necessary sample suspensions of predetermined concentration for transfer to the testing apparatus of the instrument. Liquids must be pumped, transferred and moved between vessels and it is with such type of liquid transfer apparatus that this invention is concerned.

One type of the liquid transfer valve structure has been disclosed in U.S. Pat. No. 3,567,390 and that particularly consisted of a central element and a pair of outer elements engaged against opposite faces o the central element to sandwich same therebetween. The central element is movable relative to the other element between first and second positions. At least one measuring conduit is formed in the central element and at least a pair of ports are provided in each outer element. Each of the ports in one of the outer elements aligns with a port carried by other outer element so that two fluid paths are defined. The central member is indexed to a first position to align one measuring conduit with one of said fluid paths for reception in that one conduit of a portion of the fluid sample. The central element then is moved to a second position. By virtue of such movement, a quantity of the sample is segmented by means measuring conduit and deposited in the other fluid path for combining with a diluent introduced therein so as to deliver a precise dilution.

In the various fluid transfer valve constructions disclosed in the aforesaid patents, the segmenting passageways were oriented horizontally and further included associated therewith plural drive components that required maintenance of very close tolerances in manufacture. Failure to meet those close tolerances would result in either inaccurate alignment, movement, and the like, effecting the accurate measuring and transfer of the liquid. For example, when a leak formed in the valve, air may be drawn in with the sample being measured due to the vacuum associated with the drawing of the liquid sample. When to the extent that such air leaked replaces the volume that should be occupied by the liquid sample, the dilution ratio sought cannot be met and error results.

It would be desirable to permit such entrapped air to leave the segmented portion prior to the operation of the central element effecting such segmentation. If this is accomplished, then not only do proper dilution ratios occur but, much of the close tolerances mandatory in earlier valves may be relaxed since air leaking into the valve does not create erroneous measurements. Likewise, an arrangement that enables drainage under gravitational influence improves clearance of the valve passageways.

The trademark COULTER is a registered trademark, Registration No. 995,825, owned by Coulter Electronics, Inc. of Hialeah, Florida.

SUMMARY OF THE INVENTION

A liquid transfer valve for use in a diluting system and comprising a linearly movable valve element sandwiched between a pair of superposed parallel stationary elements for frictional movement therebetween, said stationary elements each having spaced sets of two parallel through passageways and said valve element having a pair of spaced parallel bores, said valve element being movable between a first position where said bores are aligned with one set of passageways and a second position where said bores are aligned with the other set of said passageways, and pneumatically operated drive means disposed on opposite ends of the valve element for driving same from one position to the other. Rail or restraining means are provided to limit the path of movement of said valve elements to a solely linear direction. Limit means which may include a pin and slot arrangement, are provided to control the extent of movement of said valve element properly to align the bores carried thereby with the appropriate set of passageways.

DESCRIPTION OF THE PREFERRED EMBODIMENTS

The fluid transfer valve construction in accordance with the herein invention is intended to function as a substitute valve for use in the diluting system such as employed in the apparatus disclosed in U.S. Pat. No. 3,549,994 granted Dec. 22, 1970 to Rothermel, et al. and is an improvement upon the fluid transfer valve structures disclosed in U.S. Pat., Nos. 3,567,389 and 3,567,390 issued to Coulter, et al. and to Rothermel respectively on Mar. 2, 1971, all three patents being owned by the assignee of the herein application. Reference can be made to these patents for a description of the general apparatus within which the fluid transfer valve of the invention is intended to operate and, as well to afford general information as to the functions which the transfer valve seeks to accomplish.

Accordingly, the specification of each of these patents respectively is incorporated herein to the extent required by one skilled in the art to understand the system and functions performed by the improved fluid transfer valve herein disclosed.

Generally, a fluid sample is obtained in any convenient manner. A tube or a snorkel is dipped into the sample and draws a quantity into the fluid transfer valve of the system. A minute measured part of the sample then is diluted with a predetermined quantity of diluent. The resulting suspension then is transferred to first testing apparatus of the automatic instrument wherein one or more tests or operations may be performed thereon. After the first test or series of tests are performed, a portion of the sample solution from said first testing apparatus again is drawn into the fluid transfer valve and a second dilution is performed by introduction of a predetermined quantity of diluent. The resulting suspension then is transferred to second testing apparatus where the required tests, etc., are performed.

In one embodiment of the invention disclosed herein, two diluting operations are employed and the resulting suspensions are tested by apparatus operating on the principle of U.S. Pat. No. 2,656,508. It should be understood that with regard to the instant invention, this is merely by way of illustration and does not so limit the present invention.

Figure 1:
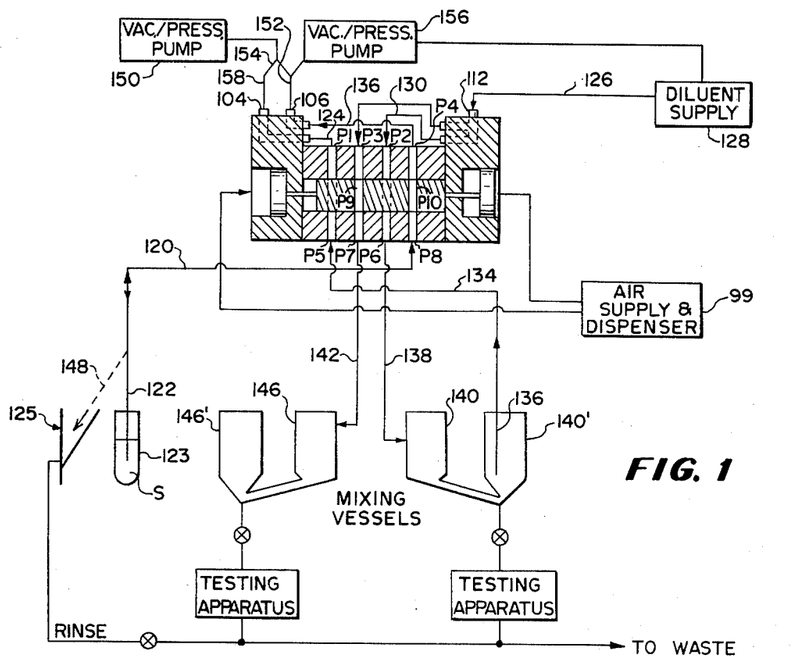
FIG. 1 is a diagrammatic representation of an automatic analysis apparatus employing the liquid transfer valve of the invention.
Figures 2, 3:
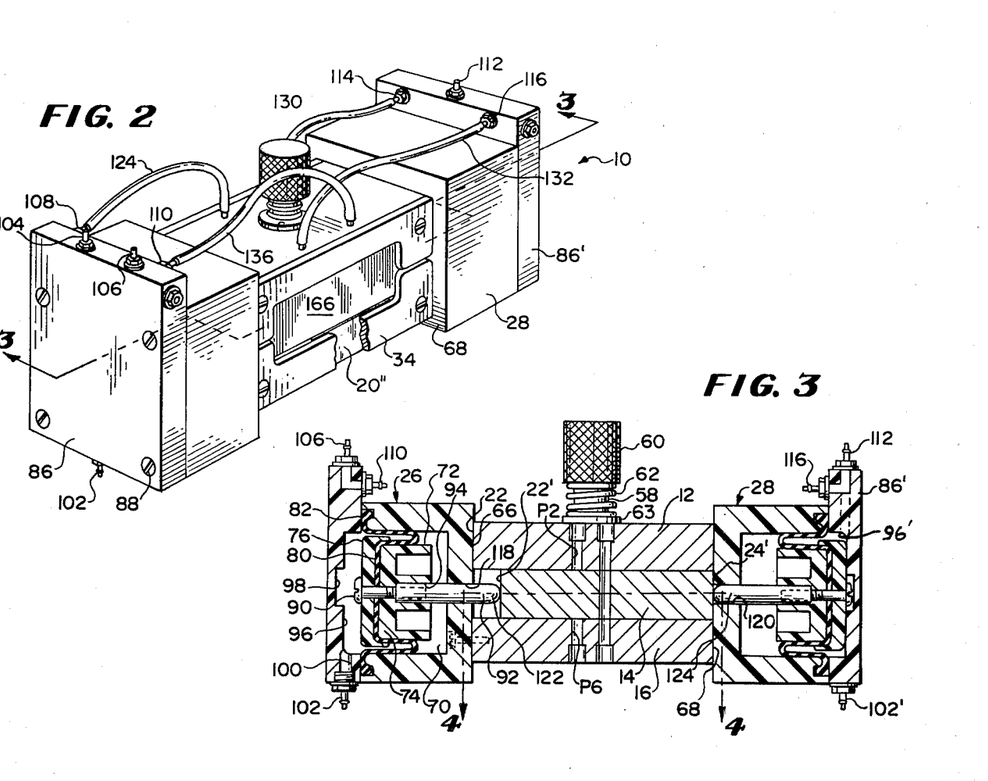
FIG 2 is a perspective view of the liquid transfer valve of the invention.
FIG. 3 is a section taken along lines 3—3 of FIG. 2 and view in the indicated direction.
Figure 4:
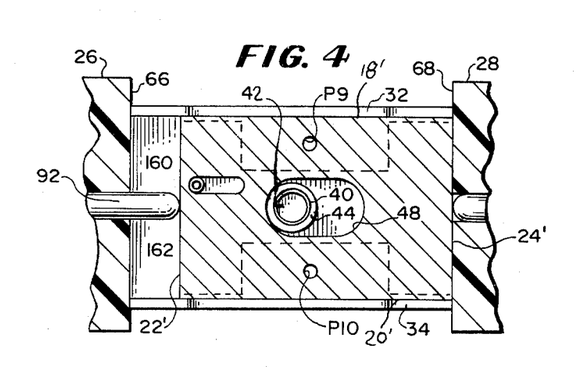
FIG. 4 is a fragmentary section taken along lines 4—4 of FIG. 3 and viewed in the indicated direction.
Figure 5:
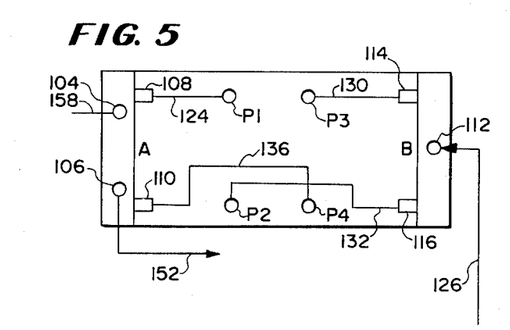
FIG. 5 is a top plan view of the valve of FIG. 2 with diagrammatic representation illustrating the conduit connections thereof to the automatic analysis apparatus.
Figure 6:
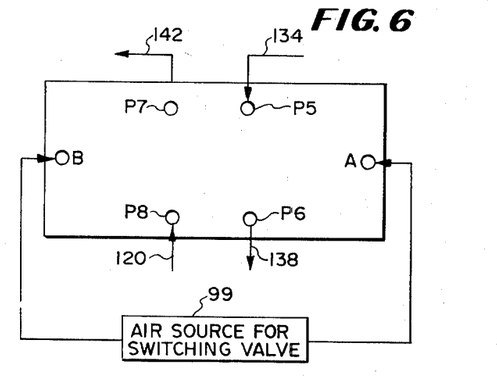
FIG. 6 is a bottom view of the valve illustrated in FIG. 2 with diagrammatic representations of the conduit connections to the automatic analysis apparatus.
Figure 7:
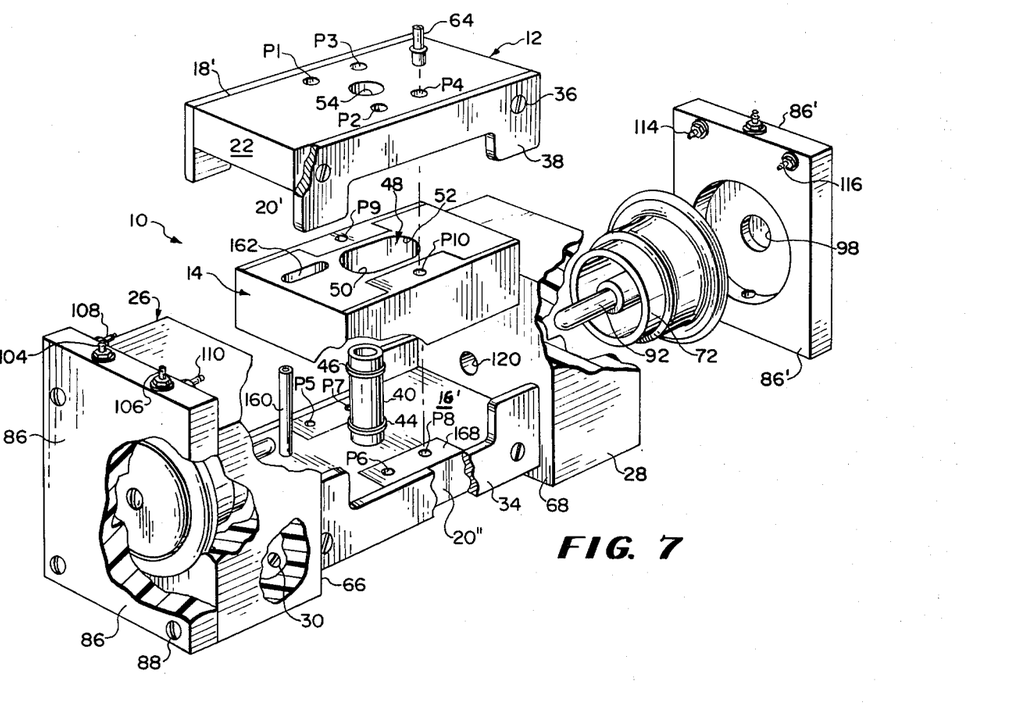
FIG. 7 is an exploded view of the valve illustrated in FIG. 2 with some portions being shown in section to illustrate interior detail.

Looking now at FIG. 1, the diagram illustrates the general diluting system connected with testing apparatus. The liquid transfer valve assembly according to the invention is coupled into the system and designated generally by reference character 10. The representation of the liquid transfer valve 10 in FIG. 1 is diagrammatic, as will be explained hereinafter. The liquid transfer valve 10 is formed of three principal elements 12, 14 and 16 with the center valve element 14 sandwiched between the two outer elements 12 and 16. The center or sandwiched element 14 is slidably movable relative to the two fixed or stationary outer elements 12 and 16 to align certain passageways.

The sandwiched or central valve element 14 of valve assembly 10 is a carefully made and highly accurate rectangular structure having bores P9 and P10 arranged adjacent opposite lineal sides 18 and 20 respectively of the central element 14. Bores P9 and P10 are axially parallel one relative to the other with their central axes lying along a plane taken normal to said lineal sides 18 and 20 and located substantially midway between the opposite ends 22 and 24 of element 14. Each of these bores P9 and P10 is designed to carry a precise quantity or volume of some liquid, and upon movement between positions, here being two such positions, will slice off or subtend within itself the said volume of liquid and pass or transfer the same. This function is represented by the arrows showing the alignment of the center bores with the passageways carried by the sandwiching stationary elements 12 and 16 of the transfer valve 10.

The outer or sandwiching elements 12 and 16 of the valve 10 are similar in configuration, both being rectangular and of equal dimension, both lengthwise and width. The width of elements 12 and 16 is identical to the width of element 14 while the length of elements 12 and 16 is greater a predetermined amount than the length of element 14. Each of elements 12 and 16 have two pair or sets of passageways formed therein and extending through the thickness thereof. These are designated P1, P2, P3, P4 in element 12, and P5, P6, P7 and P8 in element 16. The elements 12 and 16 are arranged superposed between cylinder housing 26 and 28 with the center element 14 sandwiched therebetween, the elements being in face to face engagement and with element 16 being fastened at its respective ends to the housing 26, 28 by fastening means such as screws 30 while element 12 is secured in place by means to be described. When the elements 12, 14, and 16 are assembled passageways p1 and P5 are aligned coaxially, passageways P3 and P7 are aligned coaxially, passageways P2 and P6 are aligned coaxially, and passageways P4 and P8 are aligned coaxially. Passageways P1 and P2 have axes that lie in the same plane and likewise, passageways P3 and P4 have axes that lie in the same plane. The plane passing through the axes of passageways of P1 and P2 is normal to the opposite sides 18' and 20', and the plane passing through the axes of passageways P3 and P4 is parallel to the plane taken through the axes of passageways P1 and P2. The passageways P1 and P3 are aligned along the linear distance near side 18' and passageways P2 and P4 are aligned along the linear distance near side 20'. The linear distance between the axes of passageways P1 and P3 and the linear distance between the axes of passageways P2 and P4, of course, are identical. The same relationship also applies to the passageways P5, P6, P7, and P8 to the element 16. The linear distance between the axes of passageways P1 and P3, for example, can equal the difference in length of elements 12 and 16 as compared to the sandwiched element 14. The same distance is equal to the length of the path of travel of the central or sandwiched element 14 between its two positions. The first position of the element 14 occurs when passageways P9 and P10 are aligned respectively with passageways P1, P2, P5 and P6; the second position occurring when the passageways P9 and P10 are aligned with he passageways P3, P4, P7 and P8 respectively. Identical restraining rail pairs 32 and 34 are secured on opposite linear sides 18' and 20' of element 12 and 18'' and 20'' of element 16. Securement is effected by screws 36 or similar fastening means. Each of the guide rails have restraint portions 38 which serve to restrict the movement of element 14 solely to a linear direction.

Means are provided for coupling the sandwich of elements 12, 14 and 16 in assembly without interfering with the sliding movement of element 14. A hollow cylindrical post 40 is seated in a suitable passageway 41 formed in element 16 so that its axis is normal to the surface 16' of element 16. The post 40 has a through bore 42 and is located so that its axis is midway between the ends 22'' anad 24'' of element 16 and likewise is halfway between the opposite sides 18'' and 20''. The post 40 carries annular rings 44 and 46, the purpose of which will be explained hereinafter. A through slot 48 is formed in the movable element 14, the cross section of which is generally elliptical. The major axis of slot 48 is taken along a plane parallel to the opposite lineal walls 18' and 20' of element 14 while the minor axis is coplanar with the axes of passageways of P9 and P10. The center axis of slot 48 is aligned with the center axis of bore 42. When the center element 14 is arranged in face to face engagement with element 16, the post 40 passes through the slot 48 with the ring 44 within said slot. Ring 44 reduces the bearing area. The length of the slot 48 is selected so that the movement of element 14 in a linear direction is limited to the aforedescribed predetermined distance.

In the first position of element 14, the ring 44 is engaged against one end 50 of slot 48. The second position occurs when the ring 44 bears against the opposite end 52 of the slot 48. A cylindrical passageway 54 is formed in the element 12 at a location selected to align the axis of passageway 54 with the axis of the post 40 when the elements 12, 14 and 16 are assembled. The diameter of passageway 54 is slightly greater than the outer diameter of ring 46, said ring 46 being disposed within the passageway 54 when the elements 12, 14 and 16 are assembled. The length of the post 40 is selected so that a recess is defined at the mouth of passageway 54.

A rod 58 is provided with a threaded free end which is not shown and an enlarged knurled head 60. The opposite or lower end of the interior wall of bore 42 of cylindrical post 40 is provided with a threaded socket portion. The members 12, 14 and 16 coupled tightly in assembly by introducing rod 58 through passageway 54 into the bore 42 of cylindrical post 40 and threadably engaging the threaded lower end thereof with the threaded socket portion. A helical coil spring 62 is arranged with the rod 58 passing therethrough so that spring 62 is interposed between the undersurface of head 60 and the outer surface of element 12. A washer 63 completes the assembly. When the knurled head 60 is rotated to threadably engage the rod 58 with the threaded socket and tightened, bearing against spring 62, the assembly is completed. Suitable cylindrical couplers 64 are inserted in the respective passageways carried by elements 12 and 16 so that a portion thereof projects outwardly whereby to permit conduit connections to be made thereto.

The actuator or driving means for causing the movement of the control or sandwiched element 14 are contained in the cylinder housings 26 and 28. The bodies of cylinder housing 26 and 28 are rectangular with the facing walls 66, 68 thereof parallel. Each of the cylinder housings carry the same means for actuating the movement of the central sandwiched element 14. Referring to the left-handed housing 26 as viewed in FIGS. 2–4 and 7, a chamber 70 is formed in the housing 26 and has a generally cylindrical cross section. A piston 72 comprising a pair of nested cylindrical elements 74 and 76 sandwiching a rolling diaphragm 78 is arranged within the chamber 70 for movement therewithin under the influence of air pressure. The diaphragm 78 is of hatlike configuration with the rim 80 being positively held by cover plate 86 fastened to the housing 26 as by screws 88. The portions 76 and 74 of the piston which sandwich portion 80 of the rolling diaphragm 78 are maintained in assembly by screw 90 threadably engaged with plunger 92. The plunger 92 is seated in an axial passageway or socket 94 formed in the portion 76 of the piston 72.

The cover 86 carries a socket 96 which closes off the chamber 70. A seat 98 is formed in the socket to receive the head of screw 90. A suitable bore 100 communicating to the interior of socket 96 is formed in the cover 86 and a fitting 102 is inserted therein. A pair of angular passageways is formed in the cover and suitable fittings 104, 106, 108 and 110 are secured therein to establish communication with the passageways of the valve assembly by way of flexible conduits. Cover 86' secured thereto differs from cover 86 in that only three fittings are provided; cover 86' includes a Y or T bore whose entry is indicated by fitting 112 and whose pair of outlets is indicated by fittings 114 and 116. Passageways 118 and 120 are formed respectively in the walls 66 and 68 of housings 26 and 28 respectively to permit slidable passage therethrough of the plunger ends 122 and 124. Fittings 102 and 102' communicate with suitable passageways formed in the covers 86, 86' opening to the sockets 96, 96' thereof and are coupled to lines 97, 97' leading to a supply 99 of compressed air. Air is introduced alternatively into the sockets 96 or 96' driving the respective pistons 72 or 72' in cylinders 70, 70' and thus forcing the plungers 122 or 124 against the opposite ends respectively 22' and 24' of the sandwiched member so as to place said central element 14 in one or the other of said first and second positions.

As installed in the system represented diagrammatically in FIG. 1, there are fluid lines connecting the valve assemby with the other elements of the system and these fluid connections will be explained briefly in the following discussion.

It should be understood that the fluid lines will effectively pass through pump means and control valve means some of which are not shown in the drawing. Fluid line 120 leads from the sample snorkel 122 to the passageway P8. The snorkel 122 is introduced into sample container 123.

Fluid line 126 connects the diluent supply and dispenser 128 to the fitting 112. Flexible conduit 130 couples fitting 114 to passageway P3 and flexible conduit 132 couples fitting 116 to passageway P2. Thus, passageway P3 and passageway P2 are coupled to the diluent dispenser 128. Fluid line 134 connects the white cell mixing chamber thief 136 to the passageway P5.

Fluid line 138 connects passageway P6 with the white cell mixing vessels 140 and 140'.

Fluid line 142 connects passageway P7 with the red cell mixing vessels 146 and 146'.

Fluid line 148 connects passageway P8 to waste or back to the snorkel 122 (see broken line representation 148' for rinsing thereof into a backwash receptacle 125 in broken line representation.

Fitting 106 is coupled to an alternative pressure vacuum source 150 by line 152 and by way of T connection 154 to another pump and source of diluent, both indicated by 156 to provide for the rinsing or backwash.

Fitting 104 is coupled to vacuum/pressure source 150 by line 158.

There are occasions when the elements 12 and 14 are disassembled from the assembly 10 to gain access to the bearing surfaces. Proper reassembly is essential and for that purpose, guide means are provided which comprise an upstanding post 160 secured to outer valve element 16 parallel to post 40 but offset therefrom. A narrow slot 162 is formed in the sandwiched element 14 and a socket 164 is formed in element 12 aligned with the post 160 so as to receive the same after post 160 passes through slot 162. The slot 164 generally is longer than the linear stroke of the element 14.

Sides 18 and 20 of the sandwiched element 14 may be provided with a wear resistant or antifriction hard faced ceramic coating designated by reference character 166 and, the same coating can be provided on the bearing surfaces of elements 12, 14 and 16 surrounding the respective passageways as represented by reference character 168.

Reference now will be directed to the operation of the diluting system so that the functions performed by the valve 10 is clearly understood.

If it is assumed that the transfer valve 10 is in the condition shown in FIG. 1 with the center element 14 disposed so that the solid line portions of conduits P9 and P10 are on the right are aligned with the passageways shown, a quantity of liquid sample S is drawn by snorkel 122 from container 123 into line 120 into aligned passageways P8, P10 and P4. The raw sample S fills the passageway P10. Then the center element 14 is moved to its alternate position (to the left as illustrated in FIG. 1), represented by the broken line position of the passageways P9 and P10, the volume of sample subtended will be aligned with the passageways P2 and P6.

Prior to the movement of the center element 14 to its second position, the solid portion of element 14 prevents communication between passageways P5 and P1. After movement to the left the center element is completed, then passageway P10 is aligned with passageways P2 and P6 and diluent automatically is dispensed through then aligned passageways P2, P10 and P6 to dispense a predetermined volume of diluent with the subtended volume of sample S to vessels 140 and 140' by use of line 138 where the first dilution or sample suspension of a predetermined concentration are made into vessels 140 and 140'.

Pump 150 then operates to draw fluid from chamber 140' by way of thief 136 along line 134 to passageway P5 and through passageway P9 and out from passageway P1.

A small part of the diluted sample that is withdrawn or thiefed from vessel 140' is contained in the passageway P9 at position 2. When the center element is indexed back to position 1, which realigns conduit P10 with passageways P8 and P4, a volume or plug of the first dilution is subtended and deposited in the flow path of the then aligned passageways P3 and P7, leading to the vessels 146 and 146'.

As is evident, a predetermined volume of raw sample is subtended in passageway P10 and a given volume of first dilution of the sample later is delivered to vessels 146 and 146' when the center element is moved from position 2 to position 1. At position 2, the subtended volume of raw sample is delivered to vessels 140 and 140' and thereafter the said first dilution of said raw sample is withdrawn from vessel 140 and fed to passageway P9 for later subtention and delivery.

All aspiration of samples is directed upwards of the valve passageways and all delivery is performed under the influence of gravity. Thus any entrapped air is permitted to rise from the measuring passageways P9 and P10 while drainage is under gravitational influence.

It should be understood that variations in the construction of the transfer valve of the invention are contemplated without departing from the scope of the invention as claimed.

What is desired to secure by Letters Patent of the United States is:

1. A liquid transfer valve assembly for use in a diluting system comprising, a valve element of rectangular configuration sandwiched by a pair of parallel elements of rectangular configuration, one of said valve element and pair of parallel elements being frictionally longitudinally movable slidably one relative to the other of said valve element and pair of parallel elements in a linear direction along a path taken parallel to and contiguous with the stationary one of said valve element and pair of parallel elements and within the bounds of said parallel elements;

actuator means drivably engaged to said assembly and operable to move said movable one back and forth between first and second positions;

each of the pair of parallel elements having spaced sets of parallel through passageways axially aligned one relative to the other;

said valve element carrying a pair of spaced measuring through bores, said set of spaced bores being aligned with one set of said passageways at said first position and aligned with the second set of passageways at said second position with said one set of passageways blocked off, said bores carried by said valve element having a predetermined volume so that liquid entrained in the bores at one of said first and second positions respectively is segmented and transferring for discharge at the other of said first and second positions, said valve element and each of said parallel elements being arranged in face to face surface engaged relationship with the engaged surfaces being parallel, and coupling means releasably securing the said elements in operative assembly.

2. The liquid transfer valve assembly as claimed in claim 1 and restraining means for maintaining the path of movement of said movable one solely linear.

3. The liquid transfer valve assembly as claimed in claim 2 in which valve element is movable and said restraining means comprise rails secured to said pair of parallel elements along the length thereof and on opposite sides of each, at least portions of said rails defining the path of movement of said valve element.

4. The liquid transfer valve assembly as claimed in claim 1 in which the distance moved by said movable one between said first and second positions is equal to the distance between axial centers of said first and second sets of passageways.

5. The liquid transfer valve assembly as claimed in claim 1 in which guide means are provided for limiting the extent of linear movement of said movable one to the distance between axial centers of said first and second aligned sets of passageways.

6. The liquid transfer valve assembly as claimed in claim 5 in which said guide means comprises a pin and slot coupling between said parallel elements and said valve element.

7. The liquid transfer valve assembly as claimed in claim 1 in which said actuator means comprise pneumatically actuated reciprocable piston means disposed within cylinder chambers disposed on opposite sides of said valve element.

8. The liquid transfer valve assembly as claimed in claim 6 in which said pin is hollow and said coupling means are spring biased and seated within said pin for securing the pair of parallel elements and said valve element in sandwiched assembly, said coupling means including operating means exterior of said valve.

9. The liquid transfer valve assembly as claimed in claim 1 in which there is a wear coating applied to surface portions of said sandwiching and sandwiched elements surrounding said passageways and bores respectively.

10. A liquid transfer valve for use in an automatic diluting system wherein at least two dilutions are produced from a single fluid sample, said valve comprising
a central member of rectangular blocklike configuration;
a pair of like outer members of rectangular blocklike configuration engaged frictionally against opposite faces of said central member to sandwich said central member therebetween;
means for linearly, slidably moving only said central member along a path taken parallel to and contiguous with said outer members between a first and a second position and within the bounds of said outer members;
guide means for defining a track accommodating said central member and preventing lateral movement thereof within said path;
restraint means for limiting the extent of movement of said central member in said path;
actuator means at opposite ends of the central member and capable of alternately applying driving force to said ends to urge said central member from one position to the other reciprocably,
said central member carrying a pair of parallel spaced measuring through bores; and
said outer member carrying two spaced sets of of through passageways, one set communicating with the measuring bores in one position of said central member and the other set communicating with the measuring bores in the other position of said central member.

11. The liquid transfer valve as claimed in claim 10 in which said outer and central members have the same width and said outer members are longer than the central member a distance equal to the maximum length of path traversable by said central member, said outer members being arranged superposed one over the other with said central member therebetween and the path taken thereby being contiguous to the facing surfaces of said outer members.

12. The liquid transfer valve as claimed in claim 10 in which said restraint means comprise pin and slot means formed in said outer and central members, said pin means being hollow and spring biased releasable coupling means seated in said hollow pin means, said coupling means capable of maintaining said outer and central members in assembly.

13. A liquid transfer valve for effecting a dilution in an automatic diluting system, said valve comprising:
a sandwich assembly comprising a linearly movable central member having opposite faces and a pair of like outer members of conforming configuration relative to said central member engaged in face to face relation with opposite faces of said central member to complete the sandwich assembly, the faces of said central and outer members occupying superposed parallel planes, a pair of spaced apart measuring through bores formed in the central member opening to the opposite faces thereof and having parallel axes in a plane normal to the direction of movement of the central member, means for effecting solely linear movement of said central member relative to the outer members along a path taken in a direction parallel to the opposite faces of the central member, contiguous to said faces and within the bounds of said outer members, at least a pair of through passageways formed in each outer member, each of said through passageways in one of said outer members being aligned with a matching passageway in the other of said outer members to define at least two liquid paths, means for limiting travel path length of said central member to a predetermined value to define first and second positions of said central member at the terminal ends of said path of travel, whereby at the first position of said central member, said measuring bore is in communication with one of the liquid paths and the other liquid path is blocked, at the second position of said central member said measuring bore is in communication with the other liquid path, said measuring bore having subtended a predetermined volume of liquid from said one liquid path to introduce same to the second liquid path for combining with diluent traversing same to produce the desired dilution.

14. The transfer valve assembly as claimed in claimm 13 wherein a pair of guide rails are secured to the opposite longitudinal sides of said outer members of said sandwich assembly maintaining said central member against lateral wobbling movement.

15. The traverse valve assembly as claimed in claim 14 in which each of said central and outer members of said sandwich assembly have a wear coating surrounding the opening of said bores and passageways.

16. The transfer valve assembly as claimed in claim 13 wherein bearing surfaces of said central and outer members carry a hard faced ceramic coating.

17. The transfer valve assembly as claimed in claim 16 in which said ceramic coating at least surrounds the openings of said bores and passageways.

18. The transfer valve assembly as claimed in claim 14 and said sandwich assembly includes pin and slot means whereby to define the limits of linear movement of said central member.

19. The transfer valve assembly as claimed in claim 13 and means for maintaining the central and outer valve members in said sandwiched assembly.

20. The transfer valve assembly as claimed in claim 13 in which said means for effecting linear movement of said central member comprise:

pneumatic actuating means including,
a source of fluid pressure,
a pair of cylinder housings secured respectively to said sandwich assembly at opposite ends of said pair of outer members, each said cylinder housing having a chamber defined therein,
piston means in the chamber for reciprocable movement and a plunger secured to said piston for reciprocation therewith, the plunger having a free end, said housing having passage means for accommodating said free end therethrough and located at the end of the path of movement of said central element of the sandwich assembly,
means for alternately applying fluid pressure from the source to the chamber for moving the piston means alternatively, whereby to cause the free end of the associated plunger to bear against and drive the central member linearly between said first and second positions.

21. A liquid transfer valve for use in an automatic diluting system, said valve comprising
a central member of rectangular configuration having opposite parallel faces;
a pair of outer rectangular configured members having parallel opposite faces conforming to the configuration of the respective opposite faces of the central member and engaged therewith in frictional face to face relation to form a sandwiched assembly therewith;
at least a pair of parallel measuring through bores formed in said central member;
at least two sets of parallel passageway pairs provided in each outer member, said outer members being arranged so that each of the passageway sets of one of said outer members is aligned with a matching passageway set of the other of said outer members to define at least two pairs of liquid paths;
the measuring bores and passageway sets being formed in said members oriented in a direction normal to the path of movement of said central member whereby to permit gravity influenced drain;
means for driving said central member linearly relative to said outer members along a path parallel to and contiguous with said outer members and within the bounds of said outer members and alternatively between first and second positions so that the measuring bores alternatively intercept one and the other of said pair of liquid paths;
and means limiting the travel path of said central member to a predetermined value defining said first and second positions of said central member.

22. The transfer valve as claimed in claim 21 in which said limiting means comprised pin and slot arrangement carried by said members.

23. The transfer valve as claimed in claim 22 in which said pin is carried by one of the outer members, and said slot is formed in said central member, said other outer members having a socket formed therein for receiving said pin after same passes through said slot, the length of said slot defining the extent of the linear movement of said central member.

24. The transfer valve as claimed in claim 23 and rail means defining the lineal path of movement of said central members and cooperating with said pin and slot arrangement to restrict movement of said central member to said path.

25. The transfer valve as claimed in claim 24 in which said socket comprises a through passageway, said post is hollow and a spring biased elongated member is secured therein from the exterior thereof effecting the retention of said members in sandwiched assembly.

26. The transfer valve as claimed in claim 25 and guide means for reassembly comprising a second pin and slot arrangement offset from said first-mentioned pin and slot arrangement.

27. In a transfer valve for use in a diluting system which includes a sandwich assembly formed of a pair of outer members and a central member movable relative thereto, said outer member being engaged against opposite faces of said central member, means for limiting the movement of said central member, to define first and second positions thereof, said first valve portion including; a conduit formed in said central member and arranged to open to the opposite faces thereof, a pair of ports of each of said outer members arranged such that the ports of one outer member to define two fluid paths, such that when said central member is in the first position said conduit is positioned between one pair of aligned ports, with the central member blocking the other pair of aligned ports whereby, indexing of said central member to said second position aligns said conduit with said other pair of ports while subtending an amount of said sample and depositing same in the fluid path defined thereby for combining with the diluent; said second valve portion being of like construction with regard to said first portion, and including a conduit and a pair of ports defining first and second fluid paths, such that when said central member is in the second position a specimen of the first dilution may be introduced into the conduit of the second valve portion, whereby, indexing of the central member from said second position back to the first position subtends an amount of the first precise dilution and positions same for mixing with diluent to provide the second precise dilution, the invention comprising said central member being movable only in a linear direction along a path parallel to and contiguous with said pair of outer members and within the bounds of said outer members; means defining a linear path of movement for said central member; the limiting means being interior of the sandwich assembly; means restricting movement of said central member to said path; and drive means operable from the exterior of said central member upon same to index said central member along said linear path between first and second positions.

28. In a transfer valve for use in a diluting system for providing a plurality of dilutions of differing concentration from a single fluid sample, and in which the transfer valve has a first portion for receiving and isolating therein an amount of the fluid sample and for combining said amount of sample with a first volume of a diluent to produce a precise desired first dilution; a vessel for receiving said first dilution; a second transfer valve portion coupled to said vessel for receiving and isolating therein an amount of said first dilution and for combining said amount with a second quantity of diluent to produce a precise desired second dilution; and means for introducing said fluid sample and said first dilution into the first valve portion and the second valve portion, respectively; the transfer valve including a plurality of elements in face-to-face contact, at least one of which is movable relative to the remainder of the valve between a first position and a second position, the said first valve portion including; a conduit formed in said movable element, ports defining a pair of fluid passageways in the remainder of the valve structure; whereby when said movable valve element is in said first position said conduit is in communication with one of said fluid passageways and said element blocks the other fluid passageway, indexing of the movable valve element to the second position aligns said conduit with said other fluid passageway while said conduit subtends an amount of fluid sample and positions said amount for combining with the diluent to produce the first precise desired dilution; the invention comprising:

means determining a linear path of movement for said movable element along a path contiguous with said outer members and in a direction parallel thereto and within the bounds of said outer members, means limiting the linear extent of said movement, and said conduits and passageways being formed in said respective valve elements oriented parallel ones to the others and in planes normal to the direction of movement of said movable valve element.

29. In a transfer valve for use in an automatic diluting system, said valve comprising: a central member; a pair of outer members engaged against opposite faces of said central member to sandwich same therebetween; said central member being movable relative to said outer member between a first and a second position, at least one conduit formed in said central member; at least a pair of ports provided in each outer member such that each of the ports in one of said outer members aligns with a port in the other of said outer members to define at least two fluid paths; whereby, said central member may be indexed to the first position to align said one conduit with one of said fluid paths for reception in said one conduit of a portion of the fluid sample, such that movement of the central member to the second position subtends in its said conduit an amount of said sample and deposits same in the other fluid path for combining with a diluent to provide a precise dilution; the invention comprising, said central member being arranged for limited movement in a linear direction contiguous with said outer members and within the bounds of said outer members;
means for linearly moving said central member relative to the outer members in a direction normal to the opposite faces of the central member to index said central member, the axes of said conduits and passageways being normal to the direction of movement of the central member; and
stop means for limiting the path of travel of said central member to a predetermined value to define said first and second positions of said central member at the terminal ends of said path of travel.

30. For use in a diluting system, a liquid transfer valve comprising at least one stationary and a movable element in juxtaposed face to face frictional contact, the movable element being linearly translatable contiguous with said stationary element between two positions relative the stationary element, each said stationary element having at least two parallel spaced sets of two spaced passageways having their axes coplanar, each set having the passageways thereof spaced a predetermined distance linearly from the passageways of the other set, means limiting the length of the path translated by said movable element to a distance equal to said linear distance and being within the bounds of said outer members, and drive means operable alternatively upon opposite ends of said movable element to move same back and forth from one position to the other.

31. The liquid transfer valve as claimed in claim 30 in which the openings of said passageway sets are surrounded by a wear-resistant ceramic coating carried by the engaged faces.

32. The transfer valve as claimed in claim 31 in which said sandwiched element is of a length less than the length of the sandwiching element by a value equal to the linear distance.

33. The transfer valve as claimed in claim 30 and guide means for constraining said sandwiched element against other than lineal movement.

34. The transfer valve as claimed in claim 31 and spring biased coupling means for holding said sandwich in assembly.

35. The transfer valve as claimed in claim 34 in which said spring biased coupling means comprise a hollow cylindrical post secured to one of the sandwiching elements, a first slot formed in the sandwiched element and a passageway formed in the other of said sandwiching elements both of size and configuration to receive said post, said hollow post having an interior threaded portion and said elongate rod means having an enlarged head and a threaded opposite end portion suitable for engagement within said post, coil spring means mounted on said rod and adapted to be compressed between said head and said other sandwiching member when said rod end is engaged with the interior threaded portion of the hollow post.

36. The transfer valve as claimed in claim 35 and second guide means within the valve for facilitating assembly of said sandwich.

37. The transfer valve as claimed in claim 36 and said second guide means comprises pin and socket means on the sandwiching elements and a second slot formed in said sandwiched element, said pin being movable within said second slot.

* * * * *

UNITED STATES PATENT AND TRADEMARK OFFICE
CERTIFICATE OF CORRECTION

PATENT NO. : 3,990,853
DATED : November 9, 1976
INVENTOR(S) : THOMAS J. GODIN

It is certified that error appears in the above-identified patent and that said Letters Patent are hereby corrected as shown below:

Col. 1, line 66, change "o" to --of--; Col. 2, line 12, change "means" to --said--; Col. 9, line 63, omit second occurrence of "of"; Col. 10, line 65, change "opening" to --openings--; Col. 12, line 31, change "of" first occurrence to --on--.

Signed and Sealed this

Twenty-sixth Day of April 1977

[SEAL]

*Attest:*

RUTH C. MASON
*Attesting Officer*

C. MARSHALL DANN
*Commissioner of Patents and Trademarks*